US00PP14341P39

(12) United States Plant Patent
van Gaalen

(10) Patent No.: US PP14,341 P3
(45) Date of Patent: Dec. 2, 2003

(54) DELPHINIUM PLANT NAMED 'DELGAAL'

(50) Latin Name: *Delphiniumn L.*
Varietal Denomination: Delgaal

(76) Inventor: Irenaeus Antonius Maria van Gaalen, Noordhoornseweg 37, 2635 GC Den Hoorn (NL)

( * ) Notice: Subject to any disclaimer, the term of this patent is extended or adjusted under 35 U.S.C. 154(b) by 71 days.

(21) Appl. No.: 09/984,617

(22) Filed: Oct. 30, 2001

(65) Prior Publication Data

US 2002/0112263 P1 Aug. 15, 2002

(30) Foreign Application Priority Data

Feb. 12, 2001 (EP) ..... 2001/0269

(51) Int. Cl.[7] ..... A01H 5/00
(52) U.S. Cl. ..... Plt./263

(58) Field of Search ..... Plt./263

(56) References Cited

PUBLICATIONS

UPOV–ROM GTITM, Plant Variety Database 2002/06 GTI Jouve Retrieval Software, Citation for Dephinium 'Delgaal'.*

* cited by examiner

*Primary Examiner*—Bruce R. Campell
*Assistant Examiner*—June Hwu
(74) *Attorney, Agent, or Firm*—Foley & Lardner

(57) ABSTRACT

A new and distinct cultivar of Delphinium plant named 'Delgaal', as described and illustrated, and particularly characterized by its green leaves, violet-blue colors, upright growth habit, terminal raceme flower arrangement with approximately 22 flowers per main stem; and inflorescence of 40 cm in length (average) and 14 cm in diameter (average).

4 Drawing Sheets

Genus and species of the plant claimed: *Delphinium L.*
Variety denomination: Delgaal.

BACKGROUND OF THE INVENTION

The present invention comprises a new and distinct cultivar of Delphinium, botanically known as *Delphinium L.,* and hereinafter referred to by the cultivar name 'Delgaal'.

The new Delphinium was discovered by the inventor in Den Hoorn, The Netherlands, in May, 2000 as a naturally occurring mutation from *Delphinium belladonna* 'V ölkerfrieden' (unpatented).

Asexual propagation of the new cultivar by tissue culture conducted at Maasdijk, The Netherlands, starting in June 2000, has shown that the unique features of this new Delphinium are stable and reproduce true to type in successive generations.

BRIEF DESCRIPTION OF THE INVENTION

Plants of the cultivar 'Delgaal' have not been observed under all possible environmental conditions. The phenotype may vary somewhat with variations in the environment such as temperature, light intensity, day length, and fertility level without, however, any variance in genotype.

The following traits have been repeatedly observed and are determined to be the unique characteristics of 'Delgaal'. These characteristics in combination distinguish 'Delgaal' as a new and distinct cultivar:

1. upright growing
2. green leaf color
3. violet-blue flower color
4. terminal raceme flower arrangement with approximately 22 flowers per main stem; and 5. inflorescence 40 cm (average) and 14 cm in diameter (average).

Of the many commercial cultivars known to the present inventor, there are no widely know comparison varieties. The most similar in comparison to 'Delgaal' is cultivar *Delphinium belladonna* 'Völkerfrieden'.

Compared to parental cultivar *Delphinium belladonna* 'Völkerfrieden' (unpatented) the flower color of 'Delgaal' is violet-blue whereas the flowers or 'Völkerfrieden' are dark blue. Another difference is that it has turned out that the lasting time of 'Delgaal' as a cutflower is some 20 percent longer than 'Völkerfrieden'.

'Delgaal' has not been observed under all possible environmental conditions. The phenotype of the new cultivar may vary significantly with variations in environment such as temperature, light intensity, and day length without any change in the genotype of the plant. The following observations, measurements and values describe the new cultivar as grown in Den Hoorn, The Netherlands in a normal glass greenhouse under average day temperatures of between 18 to 32 degrees Celsius and 10 to 18 degrees Celsius at night. No artificial lighting, photoperiodic treatments or other cultural or environmental treatments are conducted, no growth retardants are added. These conditions closely approximate those generally used in commercial practice.

BRIEF DESCRIPTION OF THE DRAWING(S)

The accompanying photographic drawings show typical flower and foliage characteristics of 'Delgaal' with colors being as true as possible with illustrations of this type. The measurements were taken in Den Hoorn, The Netherlands, in August 2001, 10 weeks after planting of tissue plants. The plants had not been pinched.

The first drawing shows a close up of a 'Delgaal' flower.

The second drawing shows a comparison between 'Delgaal' on the right, and the cultivar 'Völkerfrieden' on the left.

The third drawing shows plantings of 'Delgaal'.

The fourth drawing shows a close-up side view of a 'Delgaal' flower.

DETAILED BOTANICAL DESCRIPTION

In the following description color references are made to The Royal Horticultural Society Colour Chart (R.H.S.). The color values were determined indoors from flowers developed in a green-house in Den Hoorn, The Netherlands, in August, 2001, in Boskoop, The Netherlands.

Propagation:
- *Type.*—By vegetative cuttings or tissue culture.
- *Rooting habit.*—Freely branching.

Plant description:
- *Crop time.*—Approximately 30 weeks from rooted cutting.
- *Form.*—Narrow inverted triangle with upright growth habit.
- *Branching habit.*—Moderate; main shoots appear from base, some lateral shoots appear, bearing only flowers, no leaves.
- *Plant height.*—Average 100 cm.
- *Area of spread.*—Average: 50 cm.
- *Vigor.*—Moderate to vigorous, approximately 30–40 cm per month.
- *Stem.*—Internode length/diameter: Average: 7 cm in length (main stems, for lateral branches don't have leaves). Color: Green; RHS 143 A to 143 B. Pubescence: None. Appearance/shape: Smooth, not very glossy. Aspect: Circular. Strength: Strong.

Foliage description:
- *Arrangement.*—Alternate.
- *Quantity per flower stem.*—Main branches, average 16.
- *Length.*—Average 13 cm.
- *Width.*—Average 14 cm.
- *Aspect.*—Flat.
- *Shape.*—Pedately cleft to almost three-parted or very deeply pedately lobed.
- *Apex.*—Acute.
- *Base.*—Attenuate.
- *Margin.*—Incised to laciniate.
- *Texture.*—Smooth, dull, no pubescence.
- *Color of upper surface, young leaf.*—Green; RHS 137 A to 139 A.
- *Color of upper surface, mature leaf.*—Green, RHS 137 A.
- *Color of lower surface, young leaf.*—Green, RHS 138 A.
- *Color of lower surface, mature leaf.*—Green, RHS 138 B.
- *Petiole length.*—Average 9 cm.
- *Petiole diameter.*—Average width 2.5 mm, average height 1.5 mm.
- *Petiole color.*—Green, RHS 143 A.

Flower description:
- *Flower type/habit.*—Single, inflorescence type is raceme.
- *Natural flowering season.*—Summer (June–August).
- *Flower longevity.*—10 days as cut flower, 10–14 days on plant.
- *Quantity.*—Average 22 per main stem.
- *Number of flowering racemes per plant.*—Average 7.
- *Fragrance.*—No.

Buds:
- *Length.*—Average 4 cm (incl. spur).
- *Spur length.*—Average 2 cm.
- *Diameter.*—1 cm.
- *Shape.*—Elliptic to oval.
- *Rate of opening.*—Approximately 1 week from stage described above.
- *Color.*—Greyed-green; RHS 192 A to 192 C tipped green; RHS 143 C to 143 D.
- *Flower size.*—Average 6 cm in length and 5 cm in width.
- *Spur length.*—Average 2.8 cm.
- *Flower shape.*—Zygomorphic.
- *Flower aspect.*—Outward.

Petals:
- *Quantity.*—4.
- *Shape.*—Lower petals spathulate to flabellate, upper petals narrow spathulate to almost oblong.
- *Margin.*—Entire.
- *Length.*—Lower petals average 1.1. cm; upper petals average 1 cm.
- *Width.*—Lower petals average 5 mm; upper petals average 4 mm.
- *Texture.*—Smooth, lower petals with hairs in the centers.
- *Upper surface color.*—When opening lower petals violet blue; RHS 96 A with yellow; RHS 5 A to B, hairs in the center; upper petals violet-blue; RHS 96 A. Fully opened lower petals violet-blue; RHS 96 B with yellow hairs in the centre; RHS 5 B. upper petals violet-blue; RHS 96 A.
- *Lower surface color.*—When opening lower petals violet-blue; RHS 96 A, upper petals violet-blue; RHS 96 B. Fully opened lower petals violet-blue; RHS 96 A, upper petals violet-blue; RHS 96 B.

Sepals:
- *Quantity.*—5.
- *Shape.*—Obovate.
- *Length.*—Two lower sepals average: 2.9 cm. Two 'side' sepals average: 2.6 cm. Upper sepal average: 2.5 cm.
- *Diameter.*—Average 1.5 cm.
- *Texture.*—Smooth, dull.
- *Color upper side.*—Immature upper side: Violet blue; RHS 91 A to 92 B with green spots at the tips; RHS 138 A to 138 B. Spur violet-blue; RHS 92 B at the base and paler towards the tip. Mature: Violet blue; RHS 91 A to 92 B with green spots at the tips; RHS 138 A to 138 B. Spur violet-blue; RHS 92 B at the base and paler towards the tip.
- *Color under side.*—Immature: Violet blue; RHS 91 A to 92 B with green spots at the tips; RHS 138 A to B. Spur violet-blue; RHS 92 B at the base and paler towards the tip. Mature: Violet-blue; RHS 91 A to 92 B with green spots at the tips; RHS 138 A to 138 B. Spurs violet-blue; RHS 92 B at the base and paler towards the tip.

Stem:
- *Length.*—Average 38 mm.
- *Diameter.*—Averge 2.5 mm.
- *Surface texture.*—Smooth.
- *Color.*—Green, RHS 143 A to RHS 143 B.

Pedicels:

*Length.*—Average 6 cm.

*Width.*—1 mm.

*Angle.*—60 degrees to 70 degrees (0 degrees=straight on top of peduncle).

*Strength.*—Strong.

*Texture.*—Smooth.

*Color.*—Green; RHS 143 A to 143 B.

Reproductive organs:

*Stamens.*—Number of stamens: Average: 25.

*Anthers.*—Anther shape: Basifixed, oblong. Anther size: Average 2 mm. Anther color: Greyed-green; RHS 189 A. Pollen: Amount: Very low. Color: Approximately green-white; RHS 157 A to 157 B.

*Pistils.*—Number of pistils: 4 . Length of pistils: 1.1. cm.

*Stigma.*—Stigma shape: 2-parted. Stigma color: Green-white; approximately RHS 157 D.

*Seed.*—No observations to date.

*Pest/disease resistance/susceptibility.*—Not more susceptible to pests and diseases than other Delphinium varieties.

I claim:

1. A new and distinct cultivar of Delphinium plant named 'Delgaal', as described and illustrated herein.

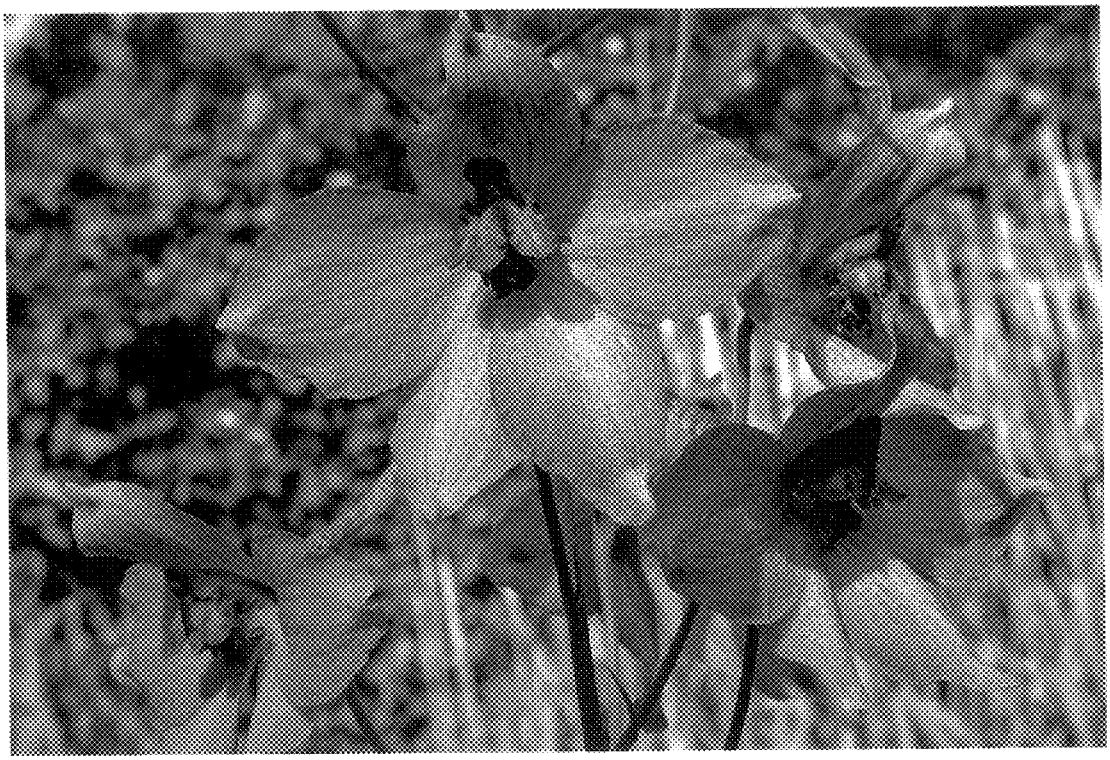

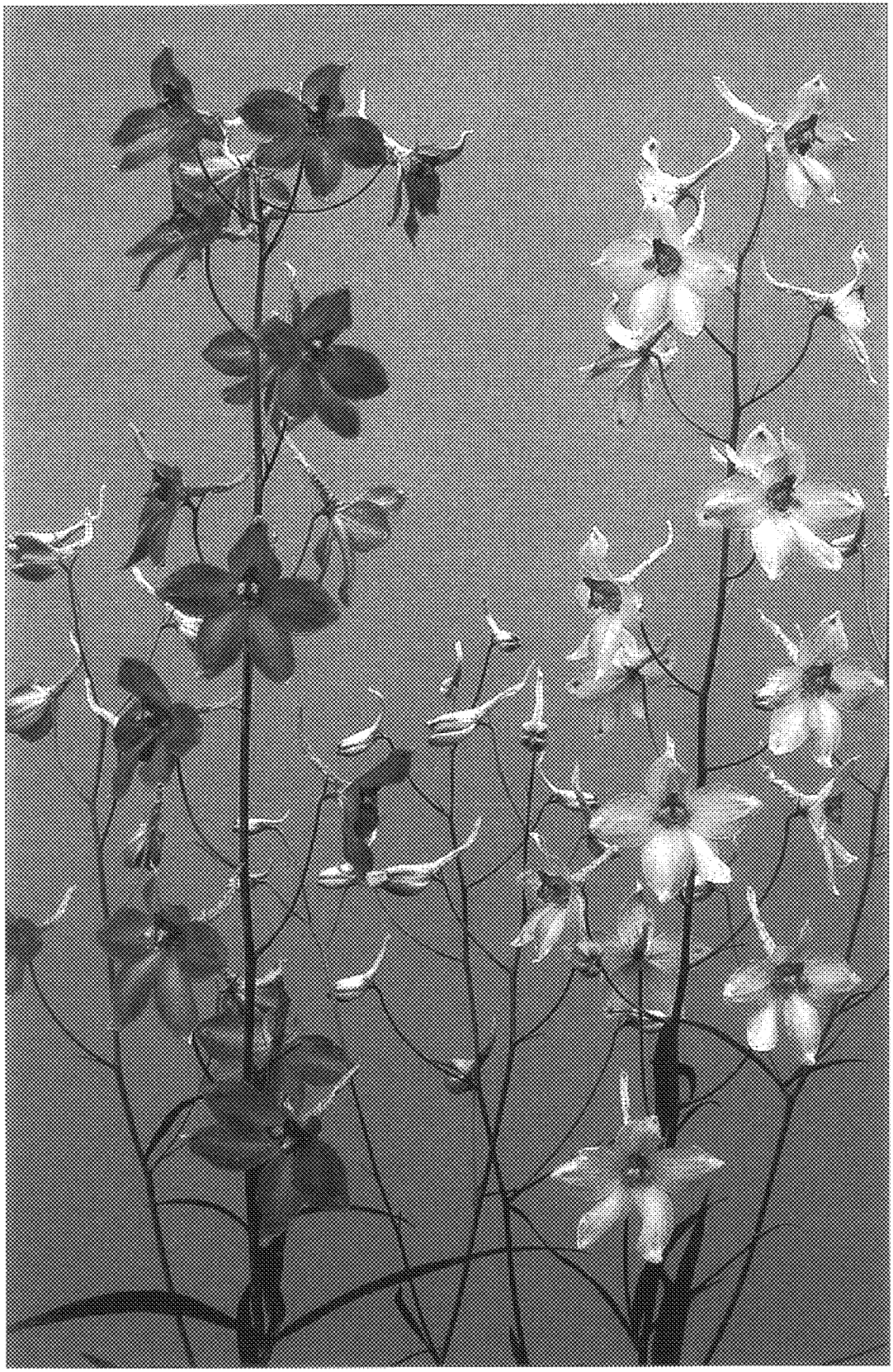

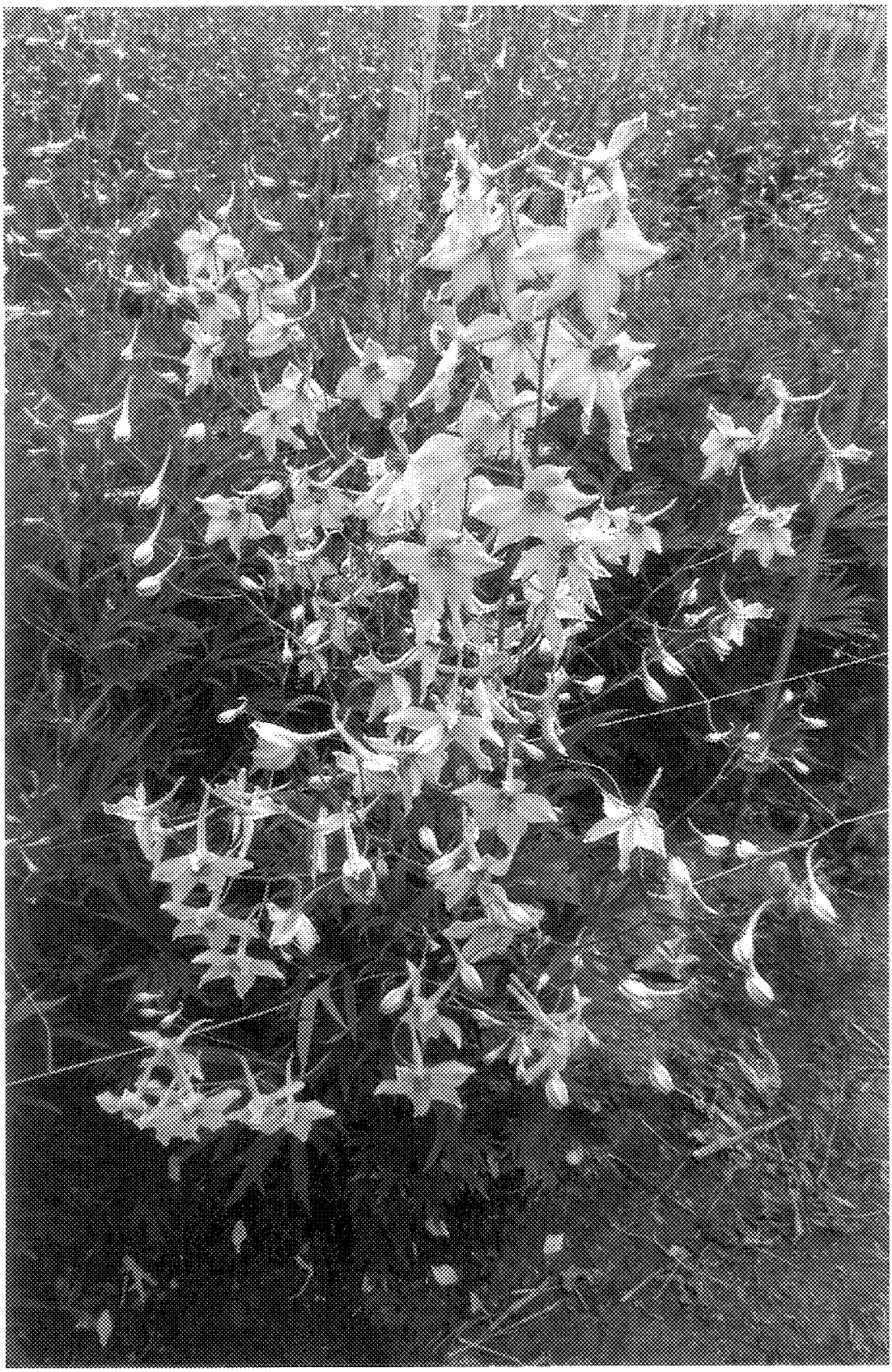

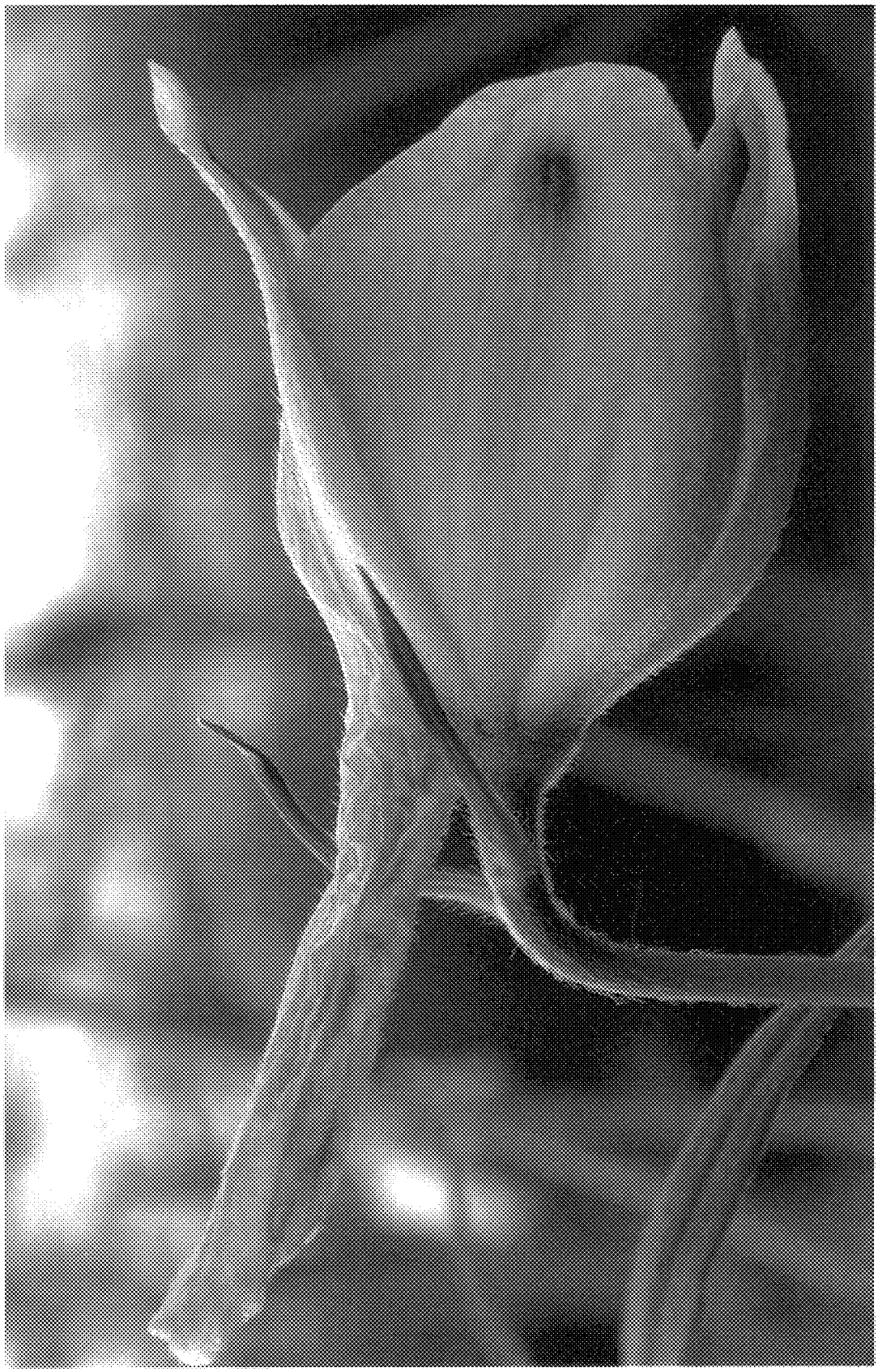

* * * * *